US012213916B2

(12) United States Patent
Patel et al.

(10) Patent No.: US 12,213,916 B2
(45) Date of Patent: Feb. 4, 2025

(54) NASOLACRIMAL DUCT STENT ASSEMBLY AND METHOD (71) Applicant: Quest Medical, Inc., Allen, TX (US)

(72) Inventors: Savan Pravin Patel, Plano, TX (US); Jeffrey John Albertsen, McKinney, TX (US); Vasu Nishtala, Frisco, TX (US); Stewart Lee Love, Herndon, VA (US)

(73) Assignee: Quest Medical, Inc., Allen, TX (US)

( * ) Notice: Subject to any disclaimer, the term of this patent is extended or adjusted under 35 U.S.C. 154(b) by 228 days.

(21) Appl. No.: 17/149,639

(22) Filed: Jan. 14, 2021

(65) Prior Publication Data
US 2021/0220175 A1 Jul. 22, 2021

Related U.S. Application Data (60) Provisional application No. 62/962,754, filed on Jan. 17, 2020.

(51) Int. Cl.
A61F 2/88 (2006.01)
A61F 9/007 (2006.01)
(Continued)

(52) U.S. Cl.
CPC ............ *A61F 9/00772* (2013.01); *A61F 2/88* (2013.01); *A61B 17/12099* (2013.01);
(Continued)

(58) Field of Classification Search
CPC .................. A61F 9/00772; A61F 2/88; A61F 2002/9505; A61F 2230/0091; A61F 2230/0013; A61F 2250/0039
See application file for complete search history.

(56) References Cited

U.S. PATENT DOCUMENTS 4,531,933 A * 7/1985 Norton ................... A61B 90/39
604/8
4,610,657 A * 9/1986 Densow .............. A61M 27/008
604/8
(Continued)

FOREIGN PATENT DOCUMENTS

CN 201164535 Y 12/2008
WO WO2006076437 A2 7/2006

OTHER PUBLICATIONS

English_Translation_Abstract_-CN201164535Y, (Dec. 2008).

*Primary Examiner* — Paul B Prebilic
(74) *Attorney, Agent, or Firm* — David W. Carstens; Stephen Y. Liu; Carstens, Allen & Gourley, LLP (57) ABSTRACT A stent for use in the nasolacrimal duct of a patient's eye. The stent is used to maintain and improve the patency of the nasolacrimal duct. The stent uses a hollow shaft to create a fluid pathway from the punctum to the inferior meatus. Either the superior or inferior punctum can be selected for insertion of the stent. An inserter is used to position the flexible stent into position. A guidewire attached to the inserter is removed from the stent and it transforms from its collapsed state to its deployed state. A first anchor stabilizes the proximal end of the stent to the punctum and ampulla. A second anchor stabilizes the proximal end of the stent near the inferior meatus. The second anchor can take any of several deployed shapes, such as a pigtail or fins.

8 Claims, 11 Drawing Sheets (51) Int. Cl.
  *A61B 17/12* (2006.01)
  *A61F 2/95* (2013.01)
  *A61M 29/00* (2006.01)

(52) U.S. Cl.
  CPC ............. *A61F 2002/9505* (2013.01); *A61F 2230/0013* (2013.01); *A61F 2230/0091* (2013.01); *A61F 2250/0039* (2013.01); *A61M 29/00* (2013.01)

(56) References Cited

U.S. PATENT DOCUMENTS

| | | | |
|---|---|---|---|
| 4,813,925 A * | 3/1989 | Anderson, Jr. | A61F 2/88 604/93.01 |
| 5,723,005 A * | 3/1998 | Herrick | A61F 9/00772 623/4.1 |
| 5,741,292 A | 4/1998 | Mendius | |
| 6,041,785 A | 3/2000 | Webb | |
| 6,238,363 B1 * | 5/2001 | Kurihashi | A61F 9/00772 606/198 |
| 6,605,108 B2 | 8/2003 | Mendius | |
| 6,629,533 B1 * | 10/2003 | Webb | A61B 17/12159 604/8 |
| 7,846,124 B2 | 12/2010 | Becker | |
| 8,192,389 B2 | 6/2012 | Fayet | |
| 8,702,643 B2 * | 4/2014 | Rapacki | A61F 9/0017 604/9 |
| 8,758,362 B2 | 6/2014 | Fayet | |
| 8,979,789 B2 | 3/2015 | Becker | |
| 9,132,088 B2 | 9/2015 | Sim et al. | |
| 9,421,127 B2 | 8/2016 | Lust et al. | |
| 10,058,451 B2 | 8/2018 | Fukaya et al. | |
| 10,300,014 B2 | 5/2019 | de Juan, Jr. et al. | |
| 2001/0053936 A1 * | 12/2001 | Whitmore, III | A61M 27/008 623/23.7 |
| 2002/0151960 A1 | 10/2002 | Mendius et al. | |
| 2005/0240277 A1 * | 10/2005 | Aliski | A61F 2/04 604/8 |
| 2007/0233037 A1 * | 10/2007 | Gifford, III | A61F 9/0008 604/93.01 |
| 2012/0089071 A1 * | 4/2012 | Oliver | A61M 27/002 604/8 |
| 2012/0116504 A1 * | 5/2012 | Lyons | A61M 31/002 623/4.1 |
| 2012/0253299 A1 | 10/2012 | Odrich | |
| 2014/0364790 A1 | 12/2014 | Matsumoto et al. | |
| 2016/0287370 A1 | 10/2016 | Rontal | |
| 2016/0367402 A1 | 12/2016 | Lim | |
| 2017/0128266 A1 | 5/2017 | Freilich | |
| 2018/0289543 A1 | 10/2018 | Silverberg et al. | |
| 2019/0117421 A1 | 4/2019 | Kahana et al. | |

* cited by examiner

NASOLACRIMAL DUCT STENT ASSEMBLY AND METHOD

CROSS-REFERENCE TO RELATED APPLICATIONS

This application claims the benefit of U.S. Provisional Application No. 62/962,754, filed Jan. 17, 2020 entitled "Nasolacrimal Duct Stent Assembly And Method," the disclosure of which is incorporated herein by reference.

TECHNICAL FIELD OF THE INVENTION

The present invention relates to a stent for use in the nasolacrimal duct of a patient's eye. The duct is dilated with a probe. Next a stent is placed into the duct through a punctum with an inserter. A guidewire in the stent is withdrawn and the stent assumes a shape that helps secure the stent in place.

BACKGROUND OF THE INVENTION

The nasolacrimal duct (also called the tear duct) carries tears from the lacrimal sac of the eye into the nasal cavity. The duct begins in the eye socket between the maxillary and lacrimal bones, from where it passes downwards and backwards. The opening of the nasolacrimal duct into the inferior nasal meatus of the nasal cavity is partially covered by a mucosal told (valve of Hasner or *Plica lacrimalis*). Excess tears flow through nasolacrimal duct which drains into the inferior nasal meatus. This is the reason the nose starts to run when a person is crying or has watery eyes from an allergy, and why one can sometimes taste eye drops.

Figure 1:
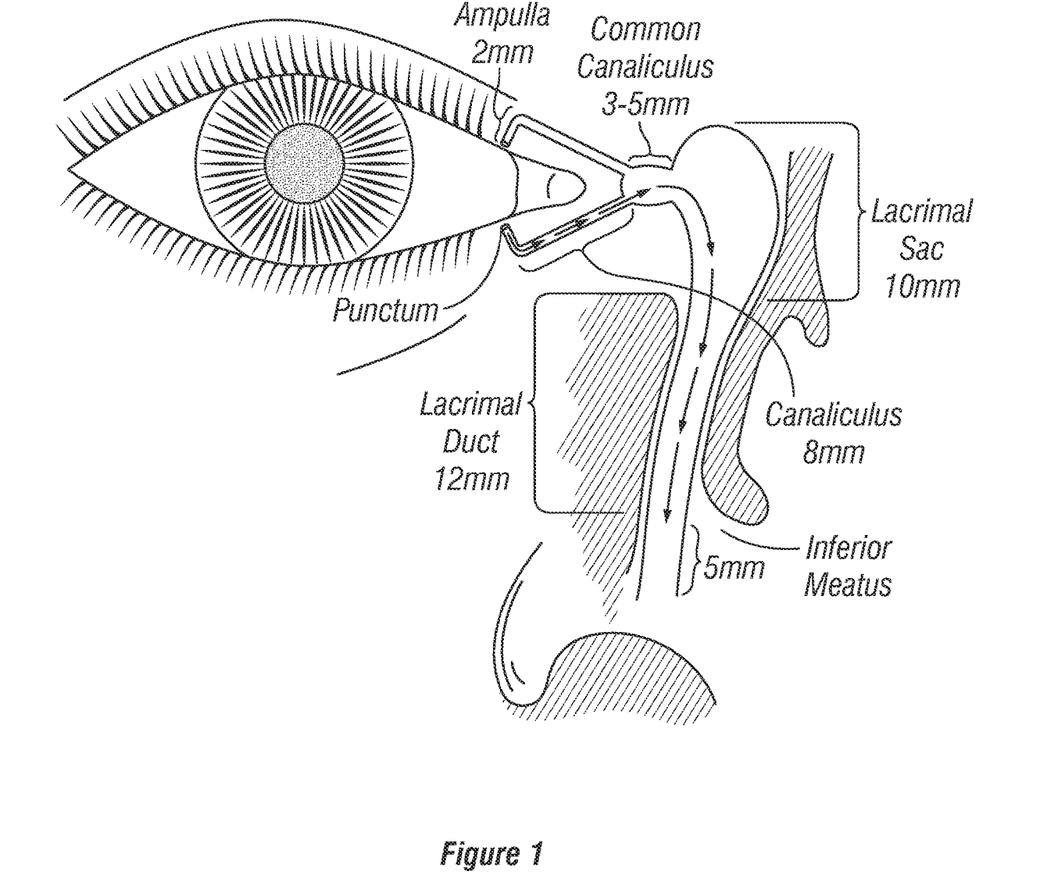
FIG. 1 is a partial sectional view of the nasolacrimal duct and adjacent anatomy.

FIG. 1 provides the general anatomy of the lacrimal drainage system. The eye has an upper and lower eyelid. The upper eyelid has a superior punctum and the lower eyelid has an inferior punctum. Each punctum is a minute opening on the summits of the lacrimal papillae, seen on the margins of the eyelids. The nasolacrimal duct can occlude, preventing the tears from properly draining into the inferior meatus. In those instances, the duct can be dilated with a probe and a stent can be placed to hold the duct open. Over a period of time, and after the duct has regained its patency, the stent can be removed.

There are a number of designs for nasolacrimal stents. For example, U.S. Pat. No. 6,238,363 discloses a device for intubation of a lacrimal duct. It involves placing plugs into both of the punctum, and then maneuvering then ends of a tube through both. The ends extend down though the lacrimal duct. A failing of this design is that it leaves an exposed portion of the tube between the two punctum. This is a distraction for the patient who will typically probe and jostle the exposed tube with their fingers. This can cause the stent to become dislodged.

A need exists for a nasolacrimal stent that has very little surface exposed to the patient. Further, a need exists for a stent that includes a means for anchoring the stent at both ends. However, any means to anchor the stent must be pliable enough to allow the stent to be removed back through the punctum.

SUMMARY OF THE INVENTION

The present invention provides an improved stent design that allows the stent to be secured on both a proximal end in the punctum and ampulla and on the distal end in the inferior meatus. Further, the present invention only presents a de minimis surface on the punctum, causing less irritation to the eye and also presenting much less exposed surface to the patient.

A patient with an occluded nasolacrimal duct will first have a probe inserted into one of the punctum. For example, a Wilder Dilator probe can be used. The probe is rotated and then forwarded through the duct to physically dilate the duct. The probe is then removed. While the duct is dilated, an inserter, loaded with the stent is used. The inserter includes a handle to allow the user to properly position the stent. A guide wire that is coupled to the inserter runs through the flexible stent and places it into a "collapsed state." The inserter can have a retractor that withdraws the guide wire from within the stent. The stent then assumes a deployed state, or shape, once the guide wire is removed. In the collapsed state, the entire length of the stent is essentially straight, making it easier to maneuver through the duct. However, the flexible stent can have a natural or deployed shape, such as a pigtail, that respond once the guide wire is removed. Many different shapes can be incorporated on the distal end of the stent.

As the stent is inserted, a flange on its proximal end is fitted into the ampulla, the circumference of the flange is larger than the punctum, thus securing the proximal end. As the guide wire is withdrawn from the placed stent, its distal end resumes its deployed state. The deployed shape is dimensioned to provide some resistance to any retraction of the stent back through the punctum. However, the level of resistance is chosen to deter but not prevent retraction.

BRIEF DESCRIPTION OF THE DRAWINGS

For a fuller understanding of the advantages provided by the invention, reference should be made to the following detailed description together with the accompanying drawings wherein.

DETAILED DESCRIPTION OF THE INVENTION

Figure 2A:
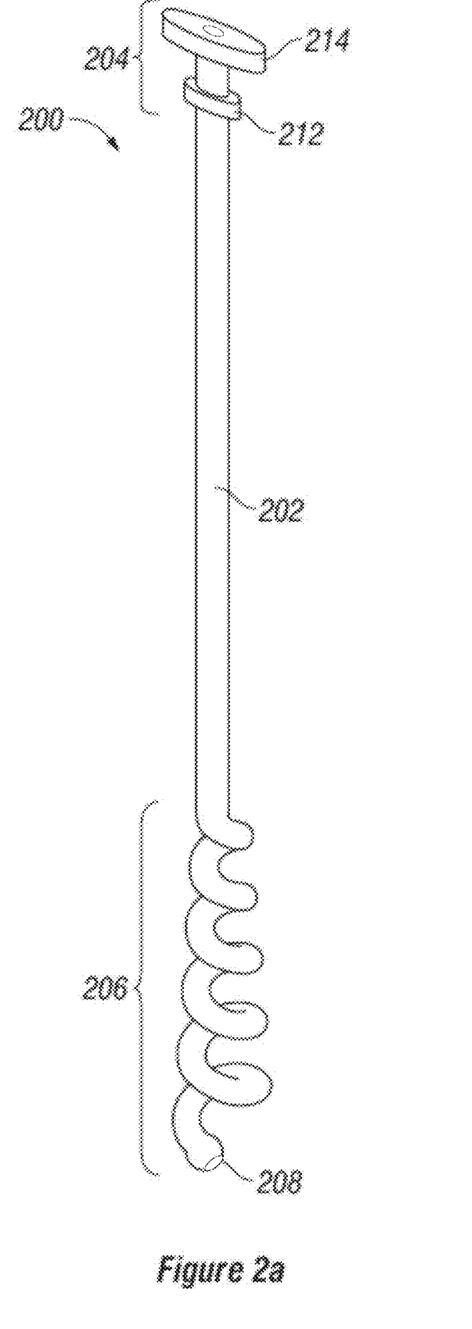
FIG. 2*a* is a perspective view of a first embodiment of the stent.
Figure 2B:
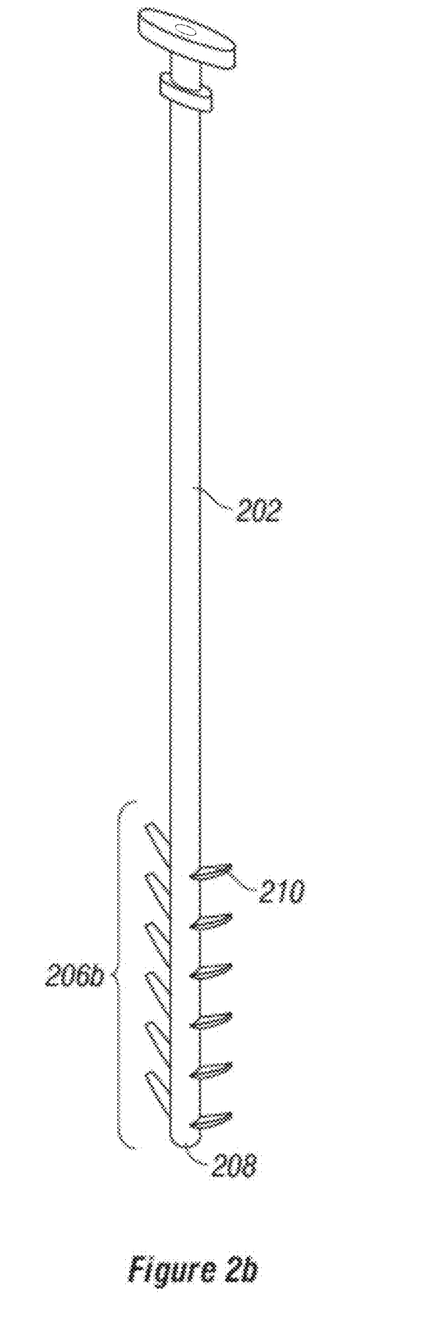
FIG. 2*b* is a perspective view of an alternative embodiment of the stent.

Referring to FIGS. 2a and 2b, a stent 200 is disclosed that embodies the present invention. The stent 200 includes a hollow shaft 202. A first anchor 204 is located on a proximal end of the shaft. The first anchor includes a punctal plug 214 and a flange 212. A second anchor 206 is located on a distal end of the shaft. The stent 200 is flexible. The second anchor, for example can have a straight or collapsed shape that allows it to be easier to insert into the duct. In this illustration, the second anchor is shown in its deployed state, which is the shape of a corkscrew. During insertion, a substantially straight guide wire (not shown) forces the second anchor into its collapsed shape. Upon removal of the guide wire, the second anchor resumes its natural or deployed state. The material selected for the stent allows for this shape memory. Note that a fluid passage extends all the way from the punctal plug 214 through the shaft 202 and to the tip 208.

FIG. 2b provides an alternative shape for the stent. The second anchor 206b is a series of bendable wings 210 that have a backwards bias. During insertion of the stent through the duct, the wings 210 deform to a collapsed position against the shaft 202. Once the distal end of the stent has passed through the duct and entered the larger inferior meatus, the wings 210 resume a deployed shape as shown. In the deployed shape, the wings 210 will resist being withdrawn back through the nasolacrimal duct. However, the wings are dimensioned such that adequate force will force them into a forward position that allows them to be pulled back through the duct once the stent is no longer needed.

Figure 3A:
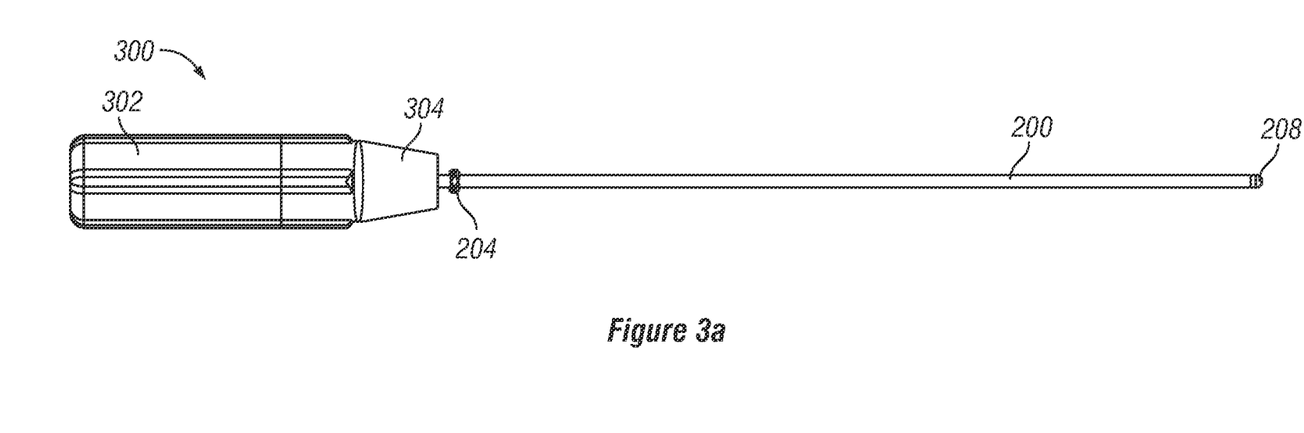
FIG. 3*a* is a side view of an inserter having a stent loaded over a guide wire.
Figure 3B:
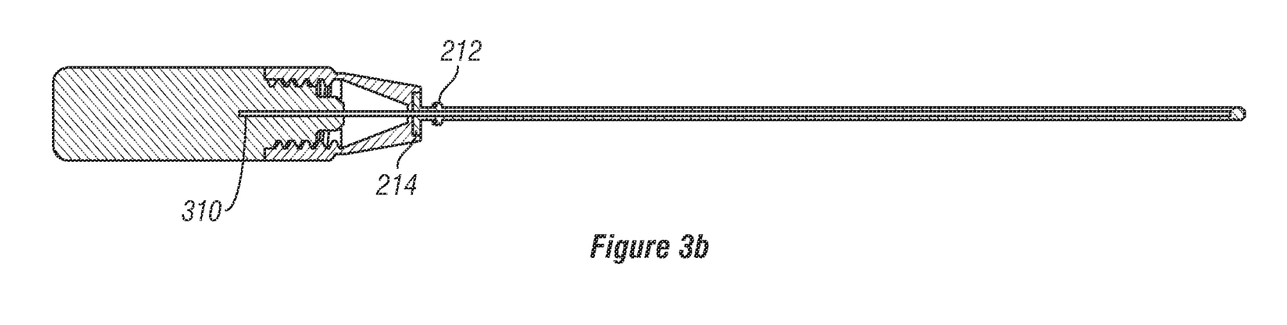
FIG. 3*b* shows a partial cut-away view of the inserter, showing the guide wire extending from a handle and through a punctum plug body and into the stent.
Figure 3C:
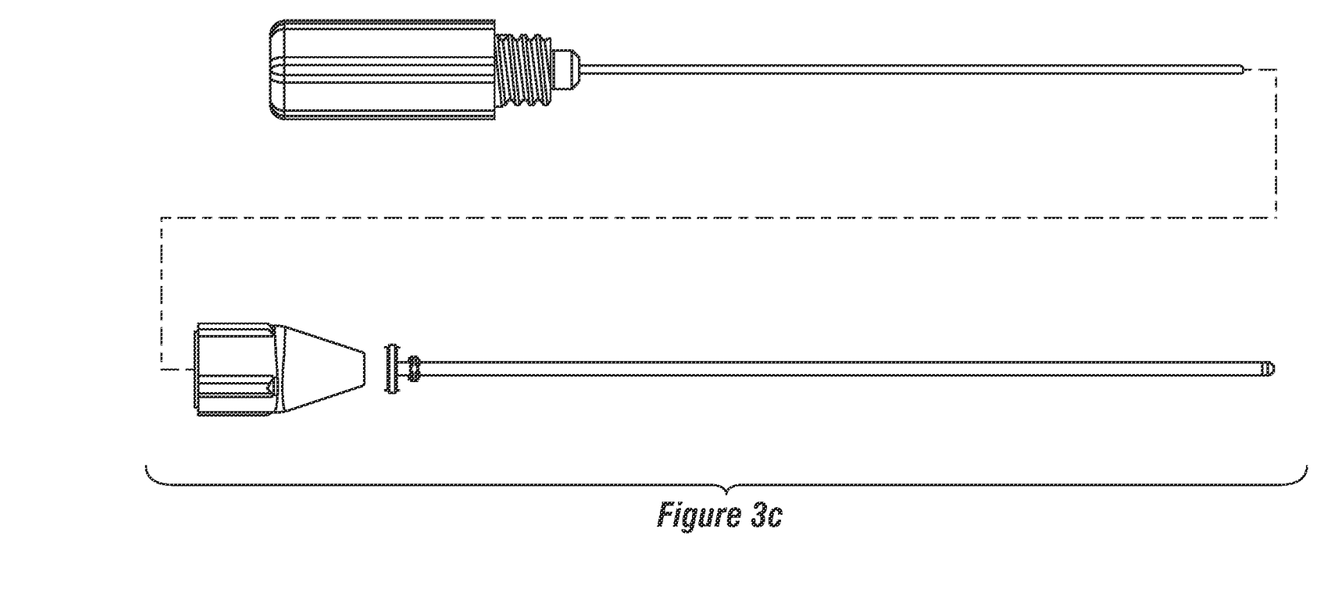
FIG. 3*c* is an exploded view of the inserter and stent assembly.

Due to the sensitive nature of the eye, it is essential to have an inserter tool that allows the user to efficiently and safely load, position, insert, set and disengage from the stent. FIGS. 3a, 3b and 3c provide an embodiment of such an inserter 300. In FIG. 3a, the inserter 300 is shown with the stent 200 engaged over a guide wire 310 (not visible). The inserter has a handle 302 that is used to position the tip 208 of the stent 200 into a selected punctum. Note that the stent is in a collapsed state, essentially straight, to make the insertion into the punctum easier. The tip 208 is designed to allow the stent to enter the punctum with little damage to the tissue. In one embodiment, the guide wire 310 extends past the tip 208 of the stent 200. However, in alternative embodiment, the guide wire 310 does not extend past the tip 208.

The inserter 300 includes a removable punctum plug body 304, shown screwed onto the handle 302 in FIG. 3b. The punctum plug body 304 can be ergonomically shaped and constructed of a flexible material to enhance control over the inserter 300. Additionally, the punctum plug body 304 may be configured to include grips at the first end and second end of the inserter 300. The flange portion 212 of the stent 200 is forward of the punctum plug body 304. After the stent is inserted into the patient's punctum, it is advanced until the flange 212 is adjacent to the punctum. It is then pressed through the punctum and into the ampulla with force applied by the punctum plug body 304. The punctum plug remains lodged in the punctum. As illustrated in FIG. 2a, the punctum plug 214 is shaped to minimize its contact with the cornea and any adjacent tissue. However, the shape shown, generally oval, can be altered and still be a part of the invention.

Figure 3D:
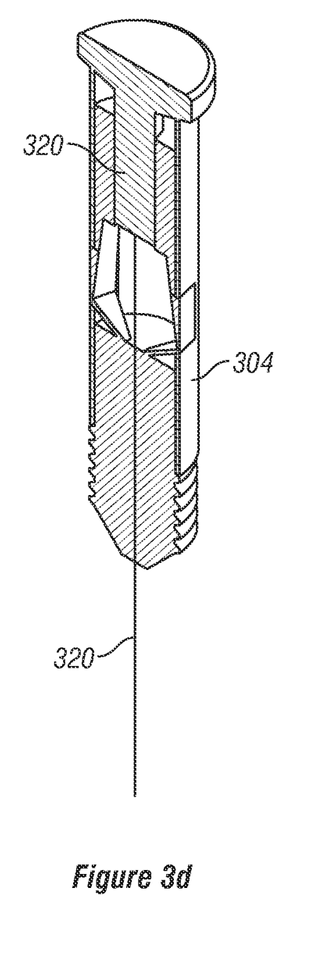
FIG. 3*d* illustrates a retraction means built into the inserter that pulls a guide wire back into the inserter handle.
Figure 3E:
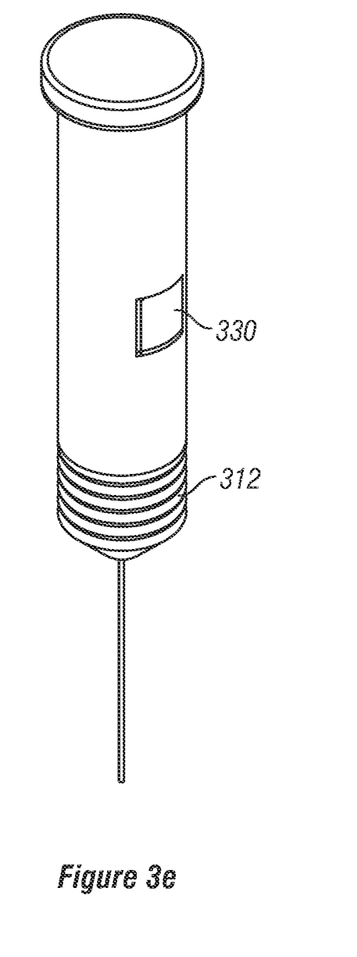

FIG. 3d provides additional detail on the guidewire 310 and its relationship with the handle 302 and punctum plug body 312. The guidewire has an extended position and a retracted position. During placement of the stent, it is extended. However, once the stent 200 is placed, it is retracted. A retraction means 320 is located in the handle 304. The retraction means is activated by a user pressing on an actuator 330 located on the outside handle 304. Upon pressing the actuator 330, the handle 302 detaches from the punctum plug body 312, which enables the user to pull the handle 302 and remove the guidewire 310. Once the guidewire 310 is completely removed, the stent 200 is implanted and the punctum plug body 312 may be removed.

Figure 4:
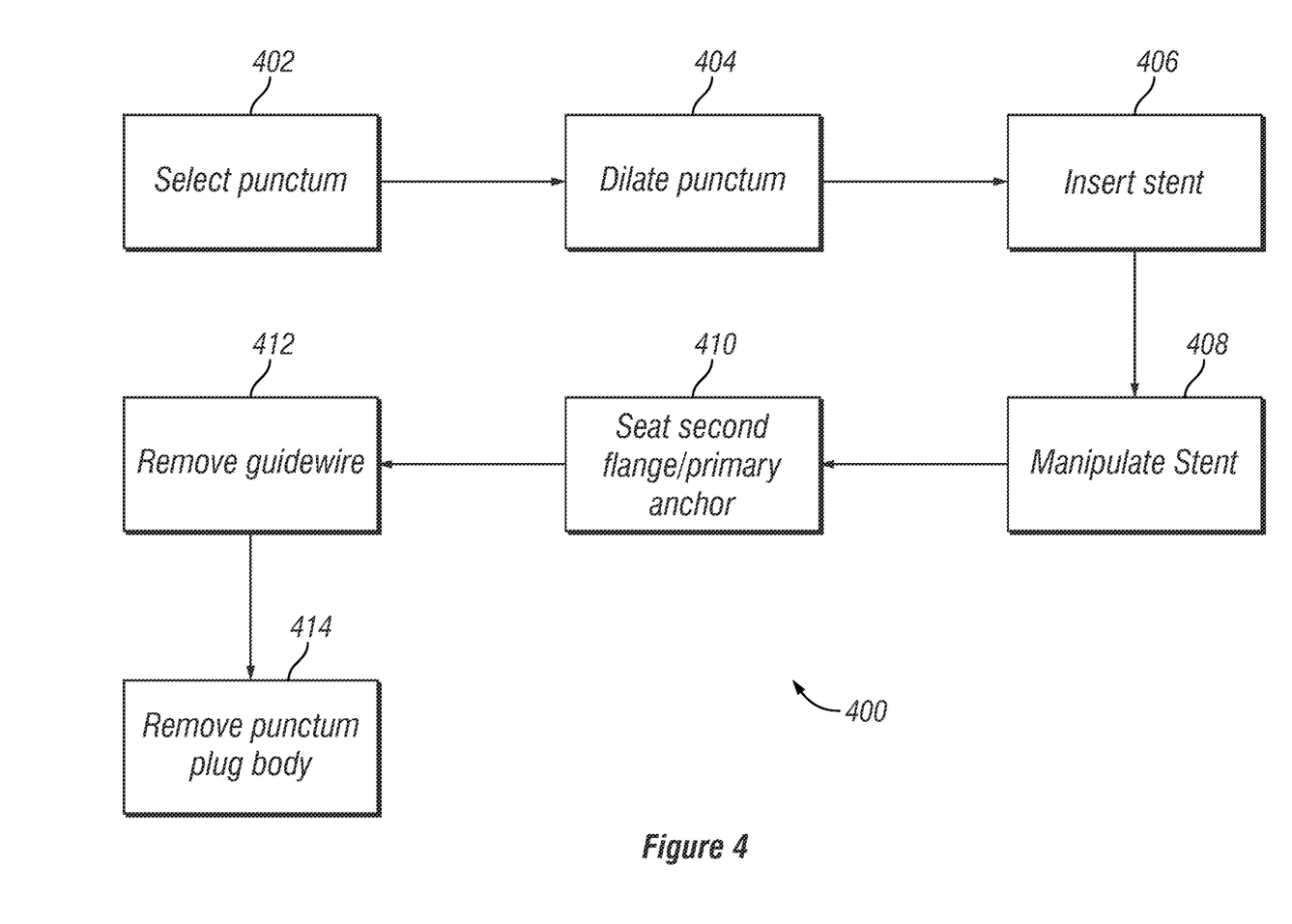
FIG. 4 provides process flow diagram for the method of setting a stent into the nasolacrimal duct.

The method of placing a stent in the nasolacrimal duct 400 involves a number of steps, generally shown in FIG. 4. As the eye has both an inferior and superior punctum, the user should select 402 which punctum to use for ingress. The punctum should be dilated 404 with a probe, such as a Wilder Dilator. The probe can be advanced all the way to the inferior meatus to ensure that the duct is adequately dilated to accept a stent. After the probe is removed, the stent, loaded on the inserter, is inserted 406 into the dilated punctum and advanced past the anatomy leading to the Valve of Hasner. Care must be exercised to not puncture through the anatomy and cause greater injury while manipulating the stent 408. The guide wire and stent are stiff enough to move through the nasolacrimal duct, but flexible enough to avoid injuring the tissue. To aid in the advancement of the stent, its surface should be smooth and covered in a lubricant. The stent can be made out of materials such as silicone or polyurethane. A hydrophilic or similar coating could also reduce the friction during insertion and removal of the stent.

The anatomy of patients varies, including the distance from the punctum to the inferior meatus. The stent is therefore only advanced until it reaches a distal surface of the inferior meatus. At that point, the user should palpate the tissue to ensure that the stent has reached its furthest point. A user could also attempt to visually confirm the stent's location by observing it through the nostril. In one embodiment, the stent has a diameter between 0.3 and 1 mm, and a length of at least 50 mm.

Once the stent is confirmed in place and the first anchor is seated 410, the guidewire is removed 412. This allows the distal end of the stent to resume its deployed state. After the guidewire is removed, the punctum plug body can be removed 414.

Figure 5A:
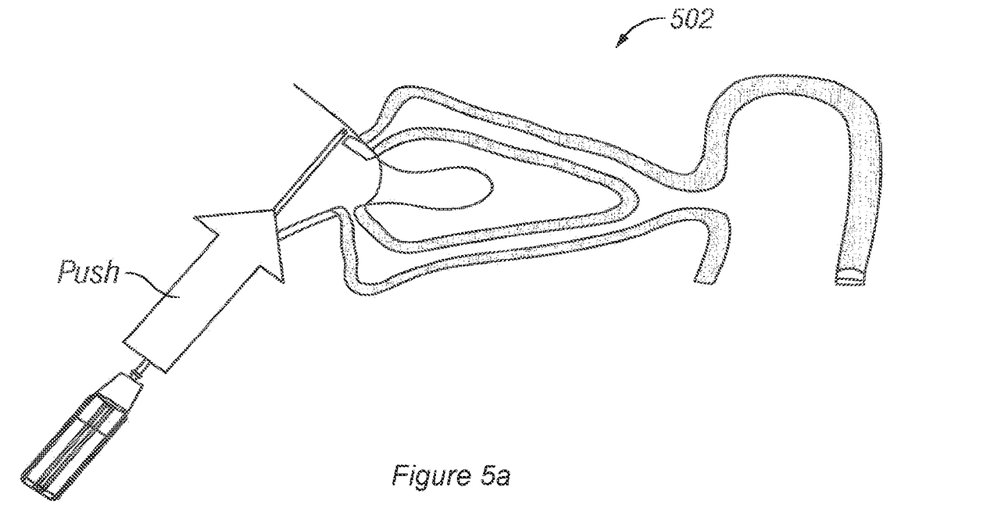
FIGS. 5*a* and 5*b* show a step-by-step illustration of the insertion of the stent into the duct, including the steps of setting a first anchor into an upper punctum.
Figure 5B:
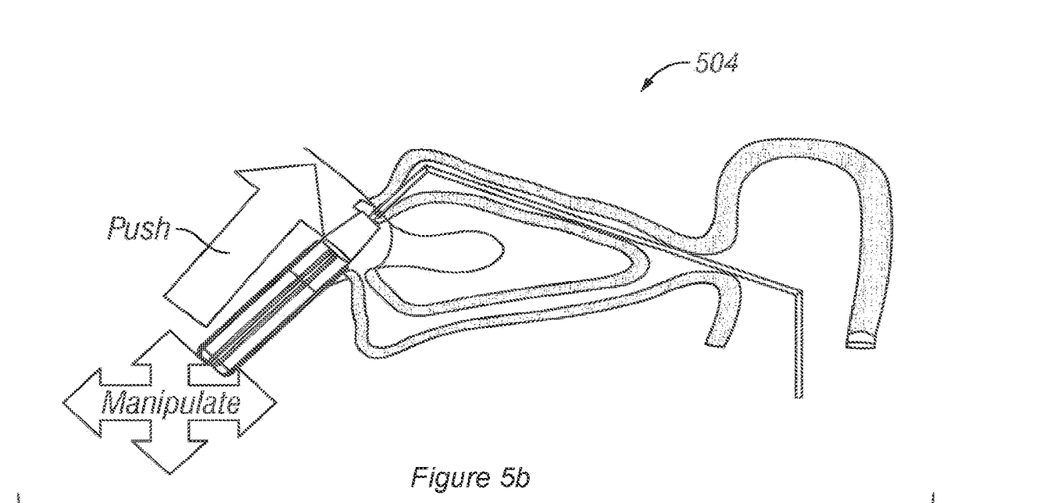
Figure 5C:
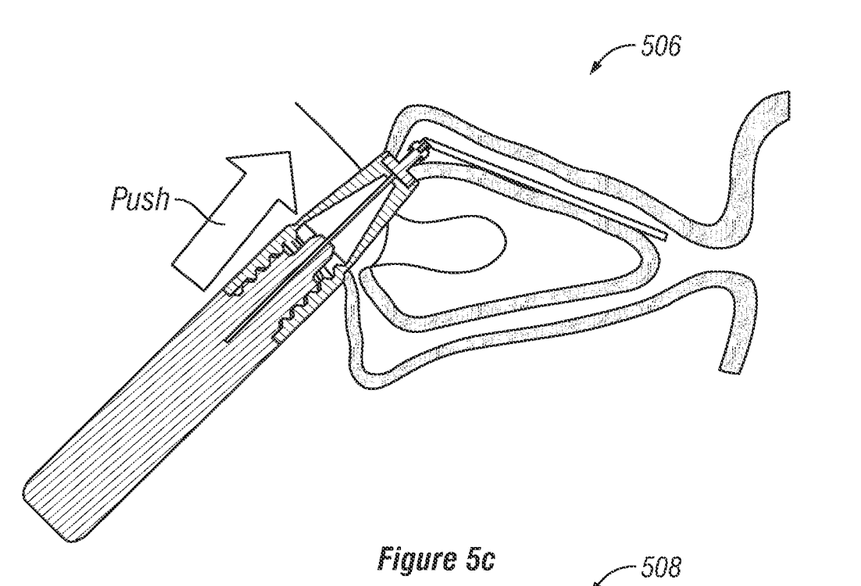
FIG. 5*c* illustrates a third step of the insertion of the stent into the duct.
Figure 5D:
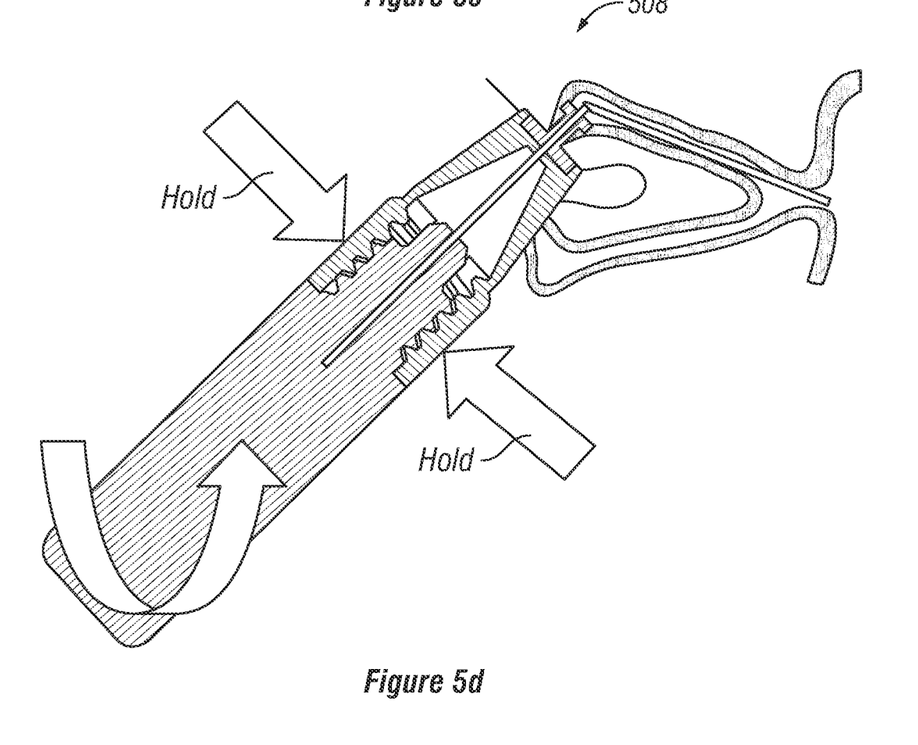
FIG. 5*d* illustrates a fourth step of the insertion of the stent into the duct.
Figure 5E:
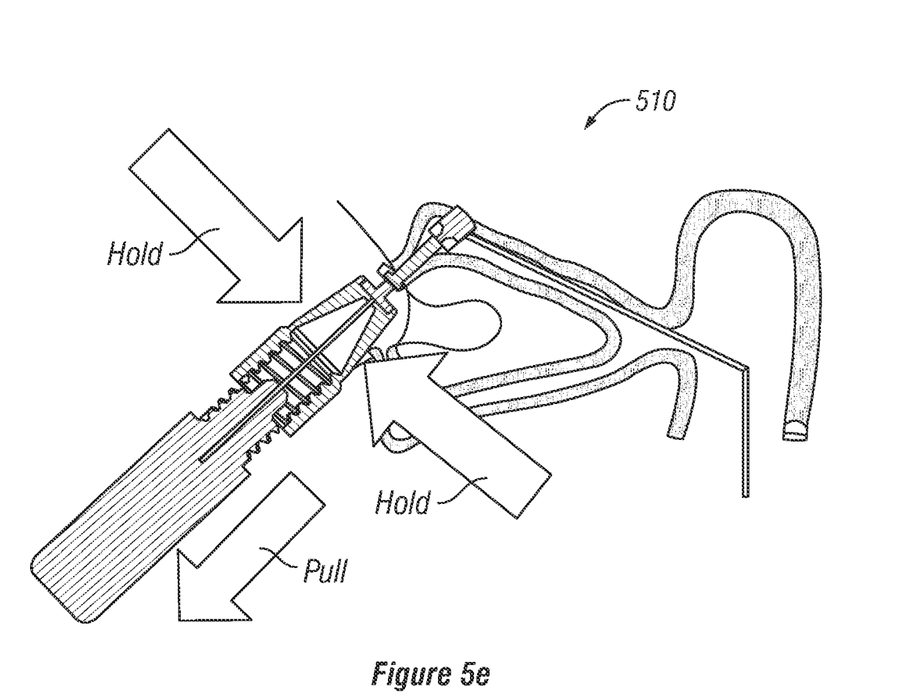
FIG. 5*e* illustrates a fifth step of the insertion of the stent into the duct.
Figure 5F:
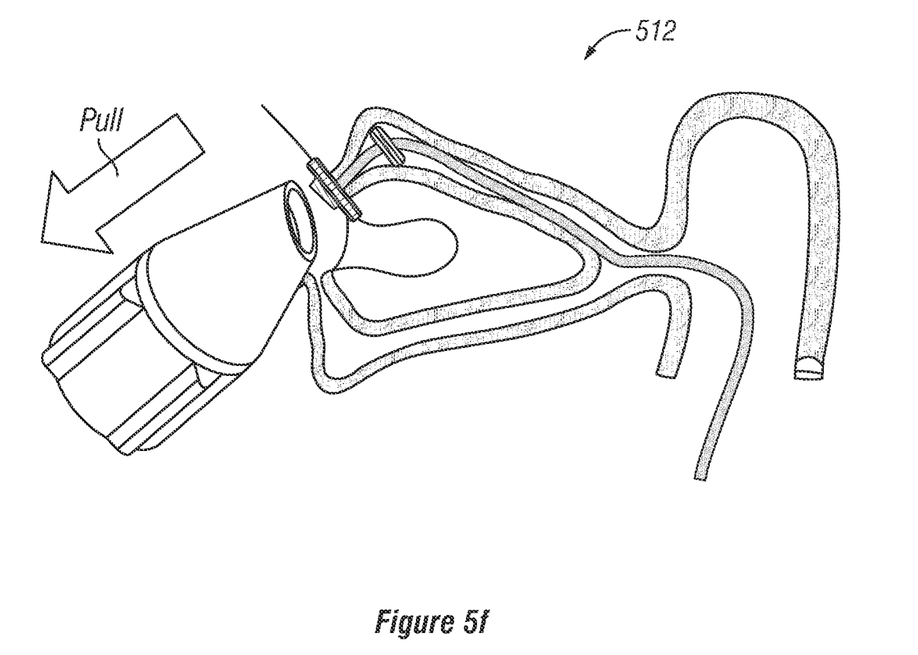
FIG. 5*f* illustrates a fourth step of the insertion of the stent into the duct.
Figure 6A:
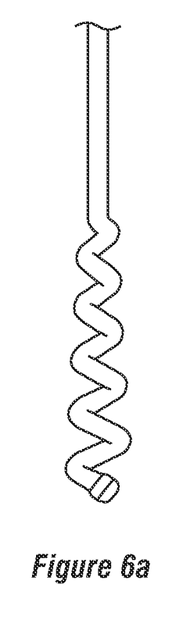
FIGS. 6*a* and 6*b* illustrate a first exemplary embodiment for the second anchor.
Figure 6B:
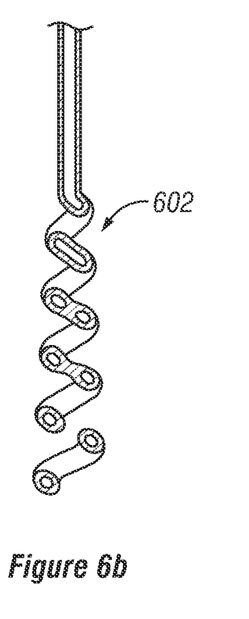
Figure 6C:
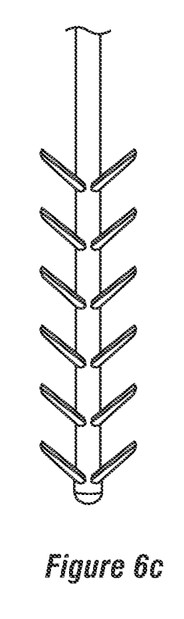
FIGS. 6c and 6d illustrate a second exemplary embodiment for the second anchor.
Figure 6D:
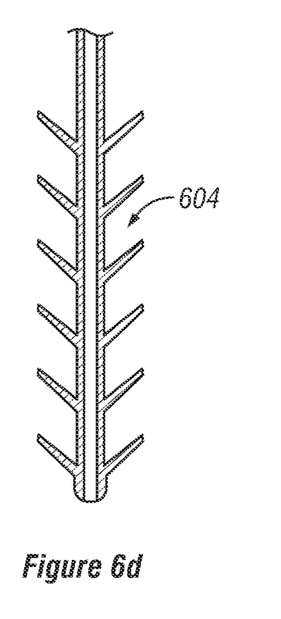
Figure 6E:
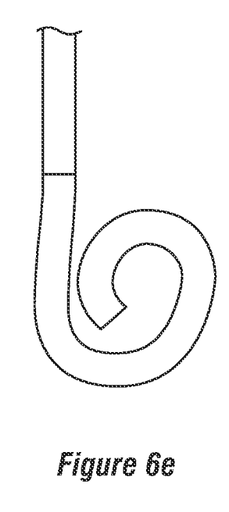
FIGS. 6e and 6f illustrate a third exemplary embodiment for the second anchor.
Figure 6F:
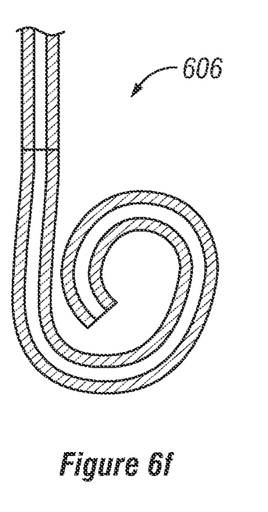
Figure 6G:
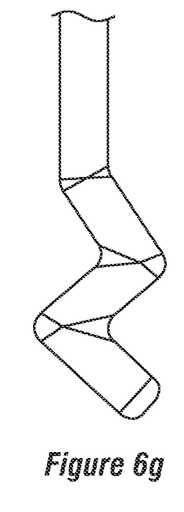
FIGS. 6g and 6h illustrate a fourth exemplary embodiment for the second anchor.
Figure 6H:
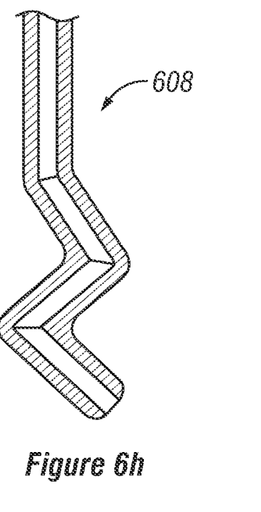
Figure 6I:
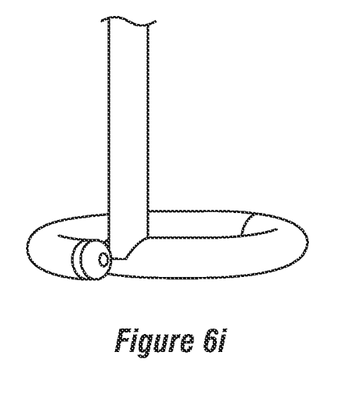
FIGS. 6i and 6j illustrate a fifth exemplary embodiment for the second anchor.
Figure 6J:
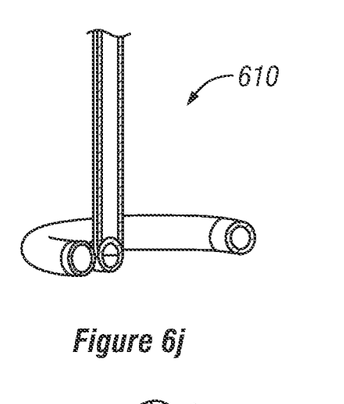
Figure 6K:
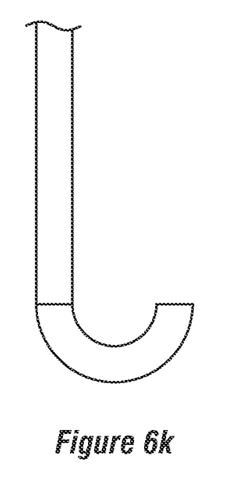
FIGS. 6k and 6l illustrate a sixth exemplary embodiment for the second anchor.
Figure 6L:
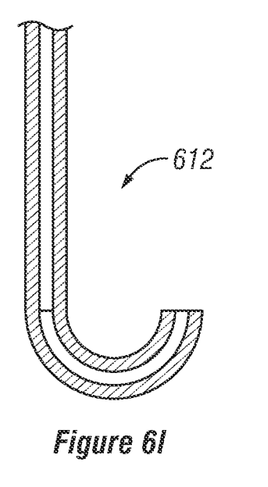
Figure 6M:
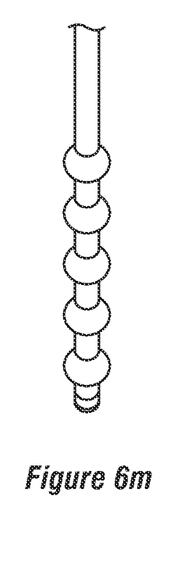
FIGS. 6m and 6n illustrate a seventh exemplary embodiment for the second anchor.
Figure 6N:
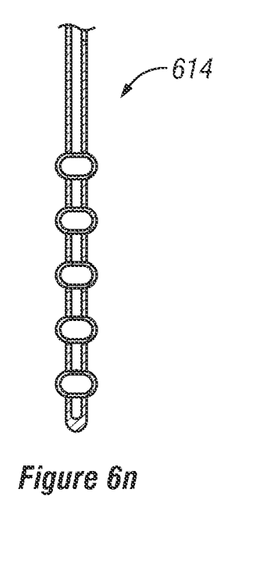
Figure 6O:
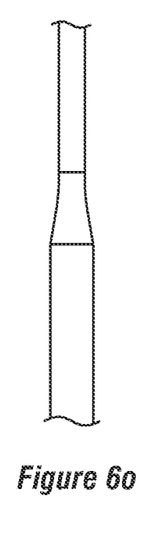
FIGS. 6o and 6p illustrate an eighth exemplary embodiment for the second anchor.
Figure 6P:
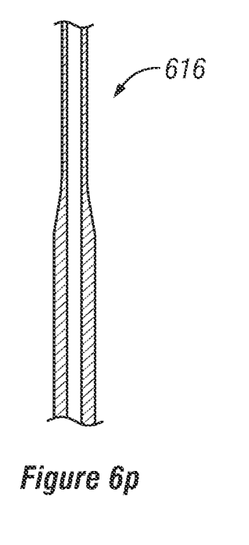

FIGS. 5a and 5b provide a graphical portrayal of an alternative process to place the stent and remove the inserter. The loaded inserter is used to push 502 the stent and guide wire into the upper punctum. The user then manipulates 504 the stent to guide it past the ampulla. The first anchor can be placed 506 into the upper punctum. Note that the anchor and stent are flexible enough to allow the guide wire to be normal to the plane of the punctum. The plug body of the inserter is held 508 by the user as the first anchor is set. The user then holds the plug body while the rest of the inserter, including the guide wire, is withdrawn from the patient 510. This leaves the plug body in the punctum, which is subsequently removed from the patient 512. The plug body provides a protective shield that prevents the guide wire from ever contacting with the eye.

FIG. 6 provides examples of various geometries that can be used for the second anchor. As discussed above, the second anchor can have a deployed state that is a corkscrew or pigtail 602. Another embodiment has a deployed state of fins 604. A third embodiment could be a curl 606. In another embodiment, the second anchor can be a zigzag 608. A fourth embodiment could be a loop or spiral 610 that is either horizontal or vertical as shown. Another embodiment could be a hook 612. A bead 614 can also be used. Finally, the second anchor could have a deployed state that comprises an increased diameter 616.

Although a preferred embodiment of the present invention has been illustrated in the accompanying drawings and described in the foregoing Detailed Description, it will be understood that the invention is not limited to the embodiments disclosed, but is capable of numerous rearrangements, modifications, and substitutions without departing from the spirit of the invention as set forth and defined by the following claims.

What is claimed:

1. A nasolacrimal duct stent, comprising:
   a hollow shaft;
   a first anchor located at a proximal end of the hollow shaft, wherein the first anchor comprises a punctal plug and a flange located forward of said punctal plug, wherein said punctal plug is sized to be lodged in a human punctum while said flange is sized to be lodged in a human ampulla internal to the punctum, the first anchor providing a fluid passage into the hollow shaft;
   a second anchor formed at a distal end of the hollow shaft, the second anchor terminating in a tip providing a fluid passage into the hollow shaft; and
   a guidewire removably positioned within the fluid passage of the first anchor, the hollow shaft, and within the fluid passage of the second anchor;
   wherein the second anchor having resiliency to hold a non-straight deployed state and having flexibility sufficient to be placed in a straight collapsed shape held via said guidewire positioned within the second anchor, said resiliency alone returning the second anchor to its deployed shape when said guide-wire is not positioned therein.

2. The nasolacrimal duct stent of claim 1, wherein the flange is further configured to stabilize the nasolacrimal duct stent to the punctum and the ampulla in the nasolacrimal duct.

3. The nasolacrimal duct stent of claim 1, wherein the hollow shaft has a length of 50 mm and a diameter between 0.3 and 1 mm.

4. The nasolacrimal duct stent of claim 1, wherein the second anchor in the deployed shape has a pigtail configuration.

5. The nasolacrimal duct stent of claim 1, wherein the second anchor in the deployed shape has a horizontal spiral configuration.

6. The nasolacrimal duct stent of claim 1, wherein the second anchor in the deployed shape has a vertical spiral configuration.

7. The nasolacrimal duct stent of claim 1, wherein the second anchor in the deployed shape has a zigzag configuration.

8. The nasolacrimal duct stent of claim 1, wherein the second anchor in the deployed shape has a hook configuration.

* * * * *